United States Patent [19]

Timmons

[11] Patent Number: 4,942,886
[45] Date of Patent: Jul. 24, 1990

[54] EXTERNAL INCONTINENCY DEVICE

[76] Inventor: John W. Timmons, 5300 Ocean Blvd., #504, Sarasota, Fla. 34242

[21] Appl. No.: 313,988

[22] Filed: Feb. 22, 1989

[51] Int. Cl.$^5$ .............................................. A61B 17/00
[52] U.S. Cl. ........................... 128/885; 128/DIG. 25; 606/157; 251/9
[58] Field of Search .................. 128/79, 171, 325-327, 128/346, 885, 886, DIG. 15, DIG. 25, 831, 843; 24/306, 442, 115 R, 257; 606/120, 142, 143, 157, 158, 201; 251/9; 604/353, 250; 600/29-31

[56] References Cited

U.S. PATENT DOCUMENTS

| 3,203,421 | 8/1965 | Biclick | 128/DIG. 25 |
| 3,866,611 | 2/1975 | Baumrucker | 128/346 |
| 4,149,540 | 4/1979 | Hasslinger | 128/327 |
| 4,534,353 | 8/1985 | de Leur et al. | 128/346 |
| 4,581,481 | 4/1986 | Moretti | 29/243.56 |
| 4,800,879 | 1/1989 | Golyakhovsky et al. | 128/325 |
| 4,822,348 | 4/1989 | Casey | 128/325 |

FOREIGN PATENT DOCUMENTS

| 2545477 | 4/1987 | Fed. Rep. of Germany | 128/79 |
| 2374 | of 1857 | United Kingdom | 128/346 |

OTHER PUBLICATIONS

Urinary Appliances, C. R. Bard catalogue, p. 22, Jan. 26, 1940.

Primary Examiner—Michael H. Thaler
Assistant Examiner—William Lewis
Attorney, Agent, or Firm—Charles J. Prescott; Raymond H. Quist

[57] ABSTRACT

An external incontinency device having first and second rigid, arcuate members hinged together at one end has a releaseable securing device at the other end. The inside of the first member is padded. A compression bar having a padded upper surface is hingedly mounted at one end to the second member. The compression bar is moveable between a position in which it will compress the uretha and a position in which the uretha is not compressed. An L-shaped lever is pivotally mounted in a slot in the second member at the juncture of its two legs. One leg extends outside the second member and serves as an operating handle. The other leg engages the compression bar to cause it to compress. Moving the handle will disengage the other leg to permit urination.

In an alternate embodiment the second arcuate member serves to compress the uretha. In this embodiment the device must be loosened to urinate.

10 Claims, 1 Drawing Sheet

EXTERNAL INCONTINENCY DEVICE

BACKGROUND OF THE INVENTION

1. Field of the Invention

This invention relates generally to external incontinency devices, and more particularly to incontinency devices of the clamp type.

2. Description of Related Art

The location of the urethra near the surface on the bottom of the penis makes the use of an external clamp an effective means of preventing incontinence. Several United States Patents disclose clamps for this purpose.

U.S. Pat. No. 3,147,754, Koessler, entitled: "Device for Controlling Incontinence", discloses a U-shaped part with a cooperating cross bar which serve as a clamp.

U.S. Pat. No. 3,155,096, Outwin, entitled: "Male Incontinence Clamp", discloses opposed pads which perform clamping.

U.S. Pat. No. 3,866,611, Baumrucker, entitled: "Incontinence Device", discloses opposed clamping surfaces with one having two spaced pressure applying devices and the other one having a single, central pressure applying device.

U.S. Pat. No. 4,534,353, de Leur et al., entitled: "Accessory for Counteracting the Consequences of Vesical Incontinence with Males", discloses a rigid, arcuate clamping member for extending across the top of the penis, with a cooperating cross bar which can be rotated between clamping and nonclamping positions.

SUMMARY OF THE INVENTION

A clamp has a first rigid, arcuate, padded member which is hinged at one end to a second rigid, arcuate member so that the free ends of these members may be moved from an abutting position to a spaced position. Extending substantially as a chord across the second member is a compression bar which is hinged to the second member near the hinge of the first and second member. An L-shaped lever having a central pivot, has one leg which serves as an operating handle, while the other leg can be moved by the handle into, and out of, engagement with the compression bar. A flexible securing strap extending from one of the members is used to hold the free ends of the first and second members in a desired relationship. A thin, flexible pinch guard is secured to one of the members on the inside to extend across the opening between the free ends of the members.

It is an object of this invention to provide an external incontinency device which can readily be closed about a penis without unduly constricting the penis.

It is another object of this invention to provide an external incontinency device permitting urination without removal.

It is also an object of this invention to provide an external incontinency device having a handle to move a compression bar to compress the urethra.

In accordance with these and other objects, which will become apparent hereafter, the instant invention will now be described with reference to the accompanying drawings.

DETAILED DESCRIPTION OF THE INVENTION

Figure 1:
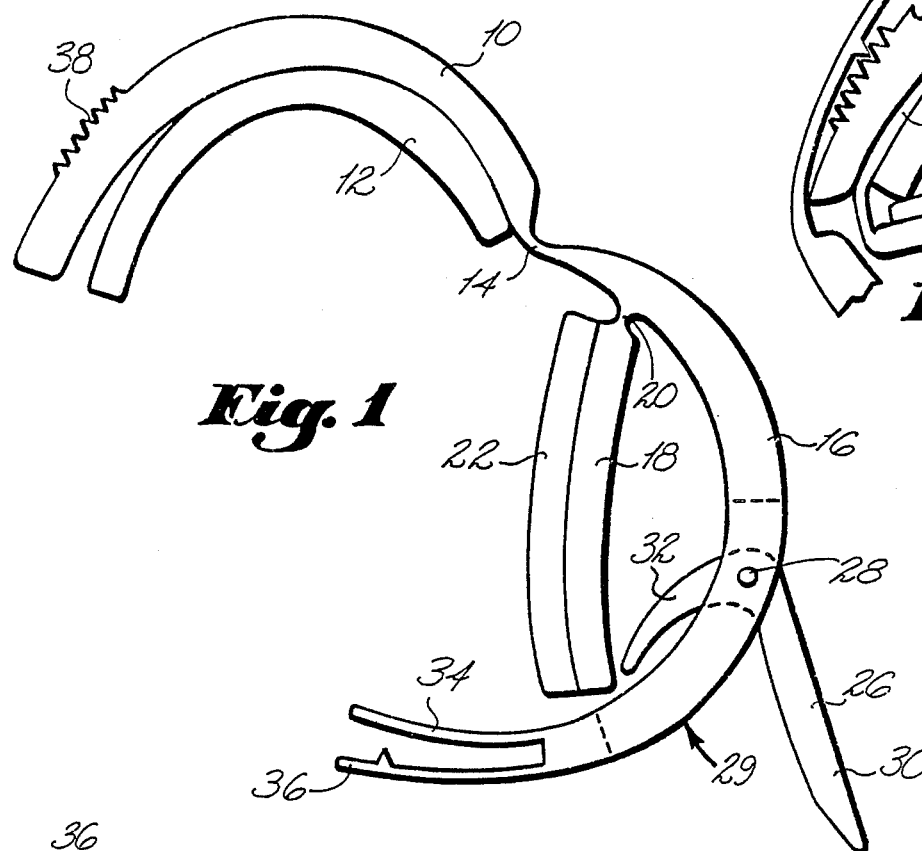
FIG. 1 is an elevation of an external incontinency device in accordance with the invention in open position.
Figure 2:
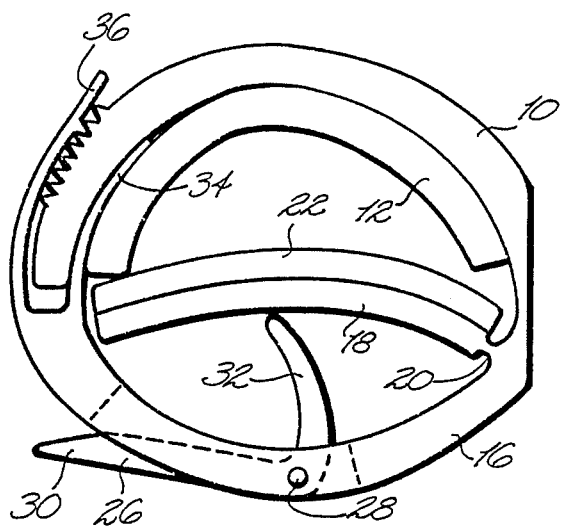
FIG. 2 is an elevation of the external incontinency device of FIG 1 in closed position. 1 in closed position.

Referring to FIGS. 1 and 2, first member 10 is arcuate in form and preferably molded of a substantially rigid material such as plastic, e.g. polypropylene. Pad 12 covers the inner surface of member 10, but is not secured thereto over the entire inner arc. At one end of first member 10, hinge 14 connects first member 10 to second member 16. Hinge 16 is formed by having a thin portion of the material. Compression bar 18 is joined to second member 16 by hinge portion 20. Compression bar 18 is somewhat arched, as shown. Pad 22 covers the upper surface of compression bar 18. Pads 12 and 22 prevent first member 10 and compression 22 from direct contact with the skin of the penis.

Lever 26 is generally L-shaped and is pivotally mounted by pin 28 in slot 29 at the juncture of the two legs. One leg is operating handle 30, and the other leg is compression bar engaging portion 32. Extending from second member 16 is one end of pinch guard 34. Pinch guard 34 extends across the gap between the free ends of first and second members 10 and 16 when these free ends move sufficiently close to each other. The free end of pinch guard 34 then extends between first member 10 and pad 12, as shown in FIG. 2. Strap 36 extends from the free end of second member 16. The end of strap 36 may be releaseably secured in any recess 38 on first member 10.

In use, with the device spread as in FIG. 1, pad 12 and first member 10 are placed on the dorsal surface of the penis. With lever 26 in the position shown in FIG. 1, second member 16 is swung up until it fits snugly. Strap 36 is then secured in a recess 38 and lever 26 is moved to the position shown in FIG. 2 which forces compression bar 18 and pad 22 against the bottom of the penis compressing the urethra. For purposes of urination, the device need not be removed - handle 30 is merely moved so that compression bar engaging portion is disengaged. The blood vessels on the dorsal side of the penis are not compressed so that the external incontinency device of this invention may be worn without stopping blood circulation. Moreover, it may readily be donned and removed, and when in the closed position does not produce a noticeable bulge in the garment of the user.

Figure 3:
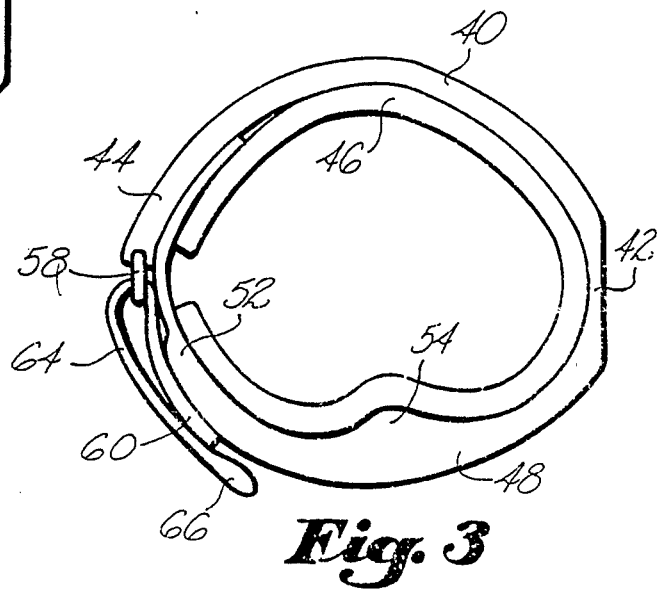
FIG. 3 is an elevation of an alternate embodiment of an external incontinency device in accordance with the invention.

Turning now to FIG. 3, an alternate embodiment of the invention will be described. Rigid arcuate member 40 has hinge portion 42 and free end 44. Pad 46 is attached to the inner surface of member 40. Rigid arcuate member 48 is secured to member 40 by hinge portion 42 and has free end 52. Member 48 has central raised portion 54 which compresses the urethra of the user when the device is donned. Pad 46 extends to be attached to the upper surface of member 48. D ring 58 is secured to free end 44 of member 40. End 60 of strap 64 is attached to the outer surface of free end 52 of member 48. Strap 64 passes through D ring 58 and is releaseably secured to end 62 of strap 64. Strap 64 has a plurality of hook elements (not shown) which are positioned to releaseably fasten to a plurality of loop elements (not shown) on end 60. Unlike the embodiment of FIGS. 1 and 2, this embodiment must be loosened for urination; however, enlarged end 66 will not pass through D ring 58.

Figure 4:
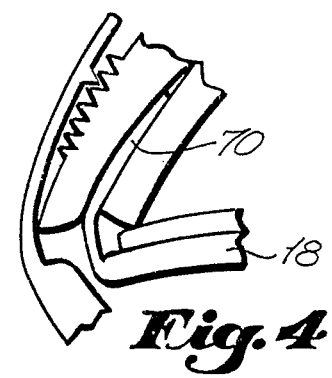
FIG. 4 is a detail showing a modification of the device of FIGS. 1 and 2.

Although the device as shown in FIGS. 1 and 2 appears to be fully operable, the modification shown in FIG. 4 is preferable from the standpoint of ease in molding. Pinch guard 70 in this modification extends from compression bar 18.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

I claim:

1. An external incontinency device comprising:
   a first rigid, arcuate member having a free end and a hinged end;
   said first arcuate member having a padded inner surface;
   a second rigid, arcuate member having a free end and a hinged end, hingedly connected to said hinged end of said first rigid, arcuate member;
   compression means including a free end and a hinged end hingedly connected adjacent to said hinged end of said first arcuate member;
   said compression means extending across said device to a point in proximity to said free end of said first arcuate member and including a rigid member having a padded upper surface; engaging means secured to said second rigid member for engaging said compression means to move said compression means to a compressing position and for disengaging said compression means to release said compression means from said compression position;
   releaseable securing means at said free ends of said first and second arcuate members for holding said free end of said first arcuate member and said free end of said second arcuate member in a desired spaced relationship.

2. An external incontinency device in accordance with claim 1 further including:
   a pinch guard extending from said second arcuate member adjacent to said free end of said second arcuate member;
   said pinch guard being a thin flexible strip, whereby said pinch guard will span any gap between said free ends of said first and second arcuate members when said device is in use.

3. An external incontinency device in accordance with claim 1 wherein:
   said first and second members have outer surfaces and said securing means is a D ring attached to one of said outer surfaces and a fabric member attached to the other one of said outer surfaces and extending therefrom;
   said fabric member having a plurality of hook elements thereon at one end positioned to releaseably engage a plurality of loop elements on the attached other end of said fabric member.

4. An external incontinency device in accordance with claim 1 wherein:
   said first arcuate member has a slot therein in which a compression bar engaging level is pivoted.

5. An external incontinency device in accordance with claim 4 wherein:
   said first and second members have outer surfaces and said securing means is a first fabric member attached to one of said outer surfaces and a second fabric member attached to the other one of said outer surfaces and extending therefrom;
   one of said first and second fabric members having a plurality of hook elements thereon positioned to releaseably engage a plurality of loop elements on the other one of said first and second fabric members.

6. An external incontinency device comprising:
   a first rigid, arcuate member having a free end and a hinged end;
   a second rigid, arcuate member having a free end and a hinged end;
   said hinged ends of said first and second arcuate members being hinged together, whereby said free ends of said first and second arcuate members can be moved from a position in which they are separated to positions in which they are spaced a desired distance;
   securing means attached to one of said arcuate members and releaseably adjusting connectable to the other of said arcuate members, whereby said free ends of said first and second arcuate members may be separated or secured in a or desired spaced position;
   a rigid compression bar having a free end and a hinged end;
   said compression bar hinged end being hinged to said second arcuate member and being movable between a compressing position and a noncompressing position extending across said device to a point in proximity with said free end of said second arcuate member;
   a lever having a pivot point mounted on said second arcuate member;
   said lever having an operating handle on one side of said pivot point and a compression bar engaging portion on the other side of said pivot point, whereby said operating handle of said lever can be moved to cause said compression bar engaging portion to move and hold said compression bar in said compressing position, and said operating handle of said lever can be moved to cause said compression bar engaging portion to disengage from said compression bar.

7. An external incontinency device in accordance with claim 6 wherein:
   said first arcuate member has an inner surface and said inner surface has a pad attached thereto;
   said compression bar has an upper surface and said upper surface has a pad attached thereto.

8. An external incontinency device in accordance with claim 6 further including:
   a pinch guard attached to said second arcuate member adjacent to said free end of said second arcuate member;
   said pinch guard being a thin flexible strip extending beyond said free end of said second member, whereby said pinch guard will span any gap between said free ends of said first and second members when said device is in use.

9. An external incontinency device in accordance with claim 6 wherein:
   said first arcuate member has an outer surface and said outer surface has a plurality of protrusion receiving recesses adjacent to said free end of said first arcuate member;
   said second arcuate member has an extension from said free end of said second arcuate member;
   said extension has a protrusion for releaseably engaging one of said protrusion receiving recesses on said first arcuate member.

10. An external incontinency device in accordance with claim 6 wherein:
    said second arcuate member has a slot therein in which said lever is pivoted.

* * * * *